Figure 1:
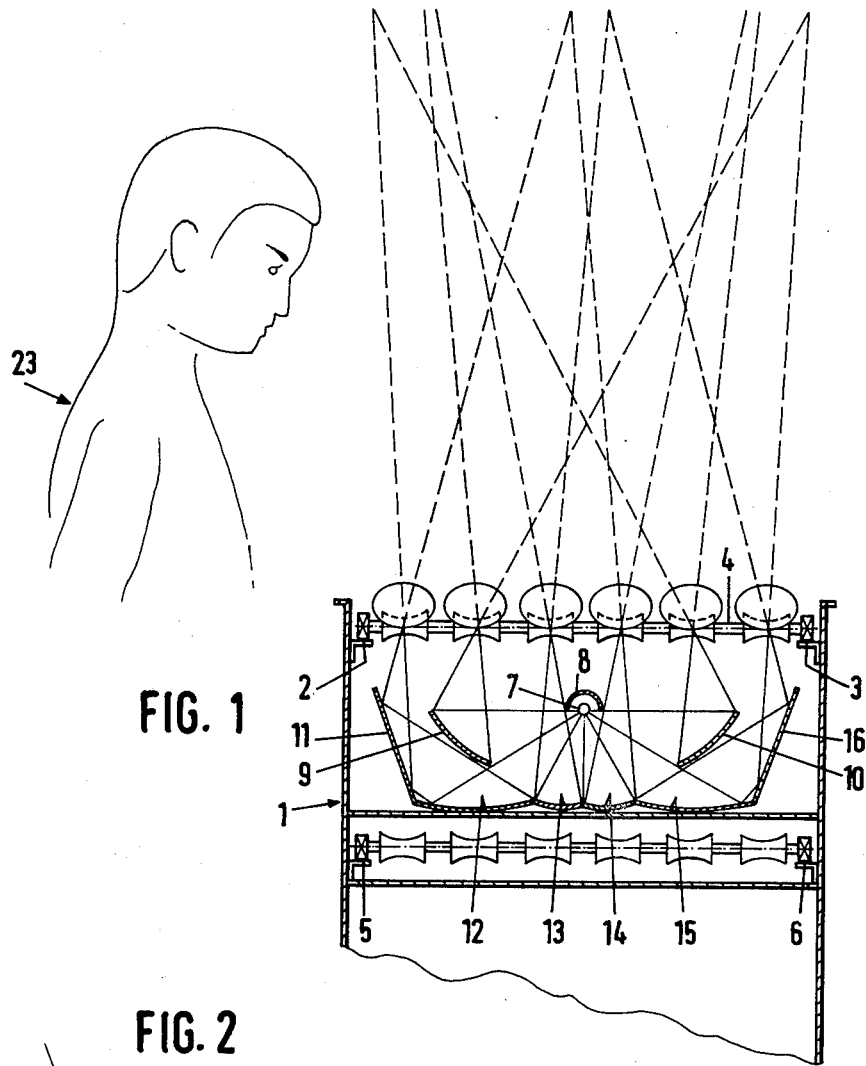

United States Patent [19]

Dewaele

[11] 4,268,168
[45] May 19, 1981

[54] EGG CANDLING DEVICE

[75] Inventor: Daniel C. C. Dewaele, Winterswijk, Netherlands

[73] Assignee: Staalkat B.V., Aalten, Netherlands

[21] Appl. No.: 962,801

[22] Filed: Nov. 21, 1978

[30] Foreign Application Priority Data

Jan. 5, 1978 [NL] Netherlands .................... 7800150

[51] Int. Cl.³ ............................................ G01N 33/08
[52] U.S. Cl. .................. 356/58; 250/223 R; 356/66
[58] Field of Search ..................... 356/52–68, 356/427–428, 239–240, 430; 250/223 R, 223 B, 572; 350/299

[56] References Cited

U.S. PATENT DOCUMENTS

| 1,023,091 | 4/1912 | Morris | 356/66 |
| 1,075,640 | 10/1913 | Foster | 356/58 |
| 2,934,995 | 5/1960 | Riesenberg | 350/299 |
| 3,027,798 | 4/1962 | Mathias | 250/223 B |
| 4,050,444 | 9/1977 | Dolamore | 350/299 |

FOREIGN PATENT DOCUMENTS

| 726499 | 3/1932 | France . | |
| 107285 | 1/1964 | Netherlands | 356/58 |
| 337645 | 11/1930 | United Kingdom | 356/66 |

Primary Examiner—John K. Corbin
Assistant Examiner—Wm. H. Punter
Attorney, Agent, or Firm—Cushman, Darby & Cushman

[57] ABSTRACT

An egg candling device comprising a partly open housing mounting guiding means for guiding a conveyor for conveying eggs in a plurality of side-by-side lanes, at least one reflector for each of said lanes, and at least one lamp disposed between said conveyor and said reflectors.

2 Claims, 2 Drawing Figures

U.S. Patent May 19, 1981 4,268,168

EGG CANDLING DEVICE

This invention relates to an egg candling device of the kind comprising a partly open housing mounting guiding means for guiding a conveyor, and illuminating means in the form of at least one lamp and at least one reflector, for the candling of eggs to be transported by means of said conveyor.

A device of this kind is described in our Dutch Patent specification No. 107,285. In it, in order to prevent the user from being dazzled, partitions are provided between the light sources and the conveyor, the side of said partitions observe to the conveyor belt being dull or diffusely reflective, and the reverse side being smooth or even a mirror surface.

As a consequence of the diffuse light produced in this prior device, a poor contrast is obtained, unless a very high light intensity is used. Furthermore, the outermost rows of eggs are subjected to a lower light flux.

It is an object of the present invention to obviate the disadvantages referred to.

To this effect, the egg candling device according to the present invention is characterized in that at least one reflector is mounted in said housing for each lane of the conveyor, and that the lamp or lamps are disposed between the conveyor and the reflectors.

According to a preferred feature of the present invention, the reflectors are constructed and arranged so that the light from the lamp or lamps is converged to the respective lanes for the eggs to be candled.

A further improvement is achieved in that the reflectors are constructed and arranged so that the light flux from the lamp or lamps is uniformly distributed over the number of lanes for the eggs. Optionally, the lamp or lamps are partly surrounded by a reflective screen.

The invention further relates to an egg candling device comprising an open-topped housing, a conveyor for conveying side-by-side rows of eggs, a lamp disposed below the level of said conveyor and surrounded at the top by a reflective screen, and a series of curved reflectors below said lamp, which, directly or via an auxiliary reflector, each collect part of the lamp flux and concentrate it on one row of eggs, the size of said reflectors, in conjunction with their position and distance from the lamp, being such that the same amount of light is projected on to each row of eggs.

Figure 2:
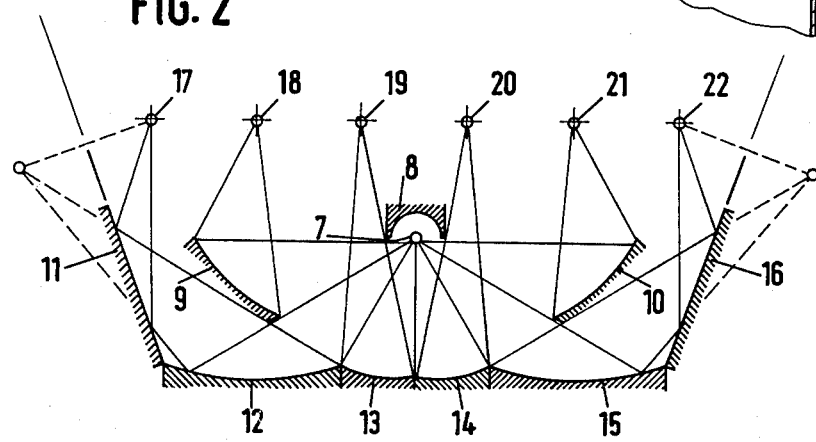

One embodiment of the invention will now be described, by way of example, with reference to the accompanying drawings, in which FIG. 1 is a cross-sectional view of an egg candling device according to the present invention; and FIG. 2 shows, diagrammatically, the lighting system used in the device of FIG. 1.

Referring to the drawings, there is shown an egg candling device comprising an open-topped housing 1 mounting guide members 2 and 3 for guiding the upper run of a known per se roller conveyor 4. Guide members 5,6 for guiding the lower run of conveyor 4 are mounted in a separate part of housing 1.

Mounted under the upper run of conveyor 4 are one or more tubular lamps 7. The light which these lamps emit upwards is reflected by a semi-cylindrical screen 8. Mounted under lamps 7 are a plurality of reflectors 9–16, disposed and arranged so that the light flux from the lamps is uniformly distributed over the various lanes (six in the embodiment shown) for the eggs.

As appears from FIG. 1, and shown diagrammatically on a larger scale in FIG. 2, reflectors 9–16 are arranged and curved so that the points 17–22 to which the light is converged are located in the lanes for the eggs. Part of the light flux from lamp 7 is concentrated via an elliptically curved reflector 12 and a plane reflector 11 in point of convergence 17; part of the light flux is concentrated via an elliptically curved reflector 13 in point 19; and part of the light flux is concentrated via an elliptically curved reflector 9 in point 18. It will be clear that the other half of the total light flux from lamps 7 is concentrated in a similar manner via curved reflectors 10, 14 and 15 and plane reflector 16 in points 20, 21 and 22, respectively.

As is further apparent from FIG. 1, an operator 23 will not be dazzled, and an ergonomically favourable construction of the device is possible.

It will be clear that many alterations and modifications can be made without departing from the scope of the present invention. Thus the elliptically curved reflectors, which in theory are optimal, may in practice be of circular or other approximate form.

I claim:

1. An egg candling device comprising a conveyor for conveying eggs in a plurality of lanes, a partly open housing mounting guiding means for guiding the conveyor, and illuminating means for the candling of eggs to be transported by means of said conveyor, the illuminating means including at least one reflector mounted in said housing for each lane of the conveyor, and at least one lamp disposed between the conveyor and the reflectors, the reflectors being so constructed and arranged as to converge the light from the lamp to respective points which are located in the respective lane for the eggs to be candled.

2. A device according to claim 1, wherein the reflectors are constructed and arranged so that the light flux from the at least one lamp is uniformly distributed over the number of lanes for the eggs.

* * * * *